US009767227B2

(12) United States Patent
Sano et al.

(10) Patent No.: US 9,767,227 B2
(45) Date of Patent: Sep. 19, 2017

(54) MATERIAL STRUCTURE PREDICTION APPARATUS, PRODUCT MANUFACTURING METHOD AND MATERIAL STRUCTURE PREDICTION METHOD

(71) Applicant: TOSHIBA MITSUBISHI-ELECTRIC INDUSTRIAL SYSTEMS CORPORATION, Chuo-ku (JP)

(72) Inventors: Mitsuhiko Sano, Tokyo (JP); Kazuhiro Ohara, Tokyo (JP)

(73) Assignee: TOSHIBA MITSUBISHI-ELECTRIC INDUSTRIAL SYSTEMS CORPORATION, Chuo-ku (JP)

( * ) Notice: Subject to any disclaimer, the term of this patent is extended or adjusted under 35 U.S.C. 154(b) by 361 days.

(21) Appl. No.: 14/634,248

(22) Filed: Feb. 27, 2015

(65) Prior Publication Data
US 2015/0178415 A1    Jun. 25, 2015

Related U.S. Application Data

(63) Continuation of application No. PCT/JP2012/072234, filed on Aug. 31, 2012.

(51) Int. Cl.
*G01N 25/02* (2006.01)
*G06F 17/50* (2006.01)
(Continued)

(52) U.S. Cl.
CPC ............. *G06F 17/50* (2013.01); *B21B 37/00* (2013.01); *C21D 9/573* (2013.01); *C21D 11/00* (2013.01);
(Continued)

(58) Field of Classification Search
CPC ...... G06F 17/50; G06F 17/5009; G06F 17/18; G06F 2217/42; C21D 11/005;
(Continued)

(56) References Cited

U.S. PATENT DOCUMENTS 5,357,443 A * 10/1994 Watanbe ................ G01N 33/20
148/541

FOREIGN PATENT DOCUMENTS

JP    5-87800 A    4/1993
JP    5-142126 A    6/1993
(Continued)

OTHER PUBLICATIONS

International Search Report Issued on Oct. 9, 2012 for PCT/JP2012/072234 Filed on Aug. 31, 2012 (English language).
(Continued)

*Primary Examiner* — Kyoung Lee
(74) *Attorney, Agent, or Firm* — Oblon, McClelland, Maier & Neustadt, L.L.P.

(57) ABSTRACT

The material structure prediction apparatus includes a temperature calculator calculating temperatures at calculation points, based on a temperature condition, a nucleation count calculator calculating a nucleation count in the calculation target region, a precipitated phase generation point determining module determining, from the calculation points, a precipitated phase generation point, a grain growth calculator calculating a grain growth of the precipitated phase at the precipitated phase generation point, and a material structure prediction module predicting the structure of the material, based on the grain growth of the precipitated phase.

20 Claims, 3 Drawing Sheets

(51) Int. Cl.
*B21B 37/00* (2006.01)
*G01N 33/20* (2006.01)
*C21D 11/00* (2006.01)
*G05B 15/02* (2006.01)
*G05D 23/19* (2006.01)
*G06F 17/18* (2006.01)
*C21D 9/573* (2006.01)

(52) U.S. Cl.
CPC ............ *C21D 11/005* (2013.01); *G01N 33/20* (2013.01); *G05B 15/02* (2013.01); *G05D 23/1917* (2013.01); *G06F 17/18* (2013.01); *G06F 17/5009* (2013.01); *C21D 2211/004* (2013.01); *G01N 25/02* (2013.01); *G06F 2217/42* (2013.01)

(58) Field of Classification Search
CPC .. C21D 9/573; C21D 11/00; C21D 2211/004; G05B 15/02; G05D 23/1917; B21B 37/00; G01N 33/20; G01N 25/02
See application file for complete search history.

(56) References Cited

FOREIGN PATENT DOCUMENTS

| | | |
|---|---|---|
| JP | 6-264137 A | 9/1994 |
| JP | 2005-297015 A | 10/2005 |
| JP | 2007-091543 A | 4/2007 |
| JP | 2012-32404 A | 2/2012 |

OTHER PUBLICATIONS

International Written Opinion Issued on Oct. 9, 2012 for PCT/JP2012/072234 Filed on Aug. 31, 2012.

Tohsiharu Morimoto, et al., "Development of Variant Analysis Program by Using EBSD Data", "Tetsu-to-Hagane" ("Iron and Steel"), published 2007, The Iron and Steel Institute of Japan (ISIJ), vol. 93, No. 9, pp. 591-599 (pp. 27-35).

Masayoshi Suehiro et al., "A Kinetic Model for Phase Transformations of Carbon Steels during Continuous Cooling", "Tetsu-to-Hagane" ("Iron and Steel"), published Jun. 1, 1987, The Iron and Steel Institute of Japan (ISIJ), vol. 73, No. 8, pp. 1026-1033 (pp. 110-117).

\* cited by examiner

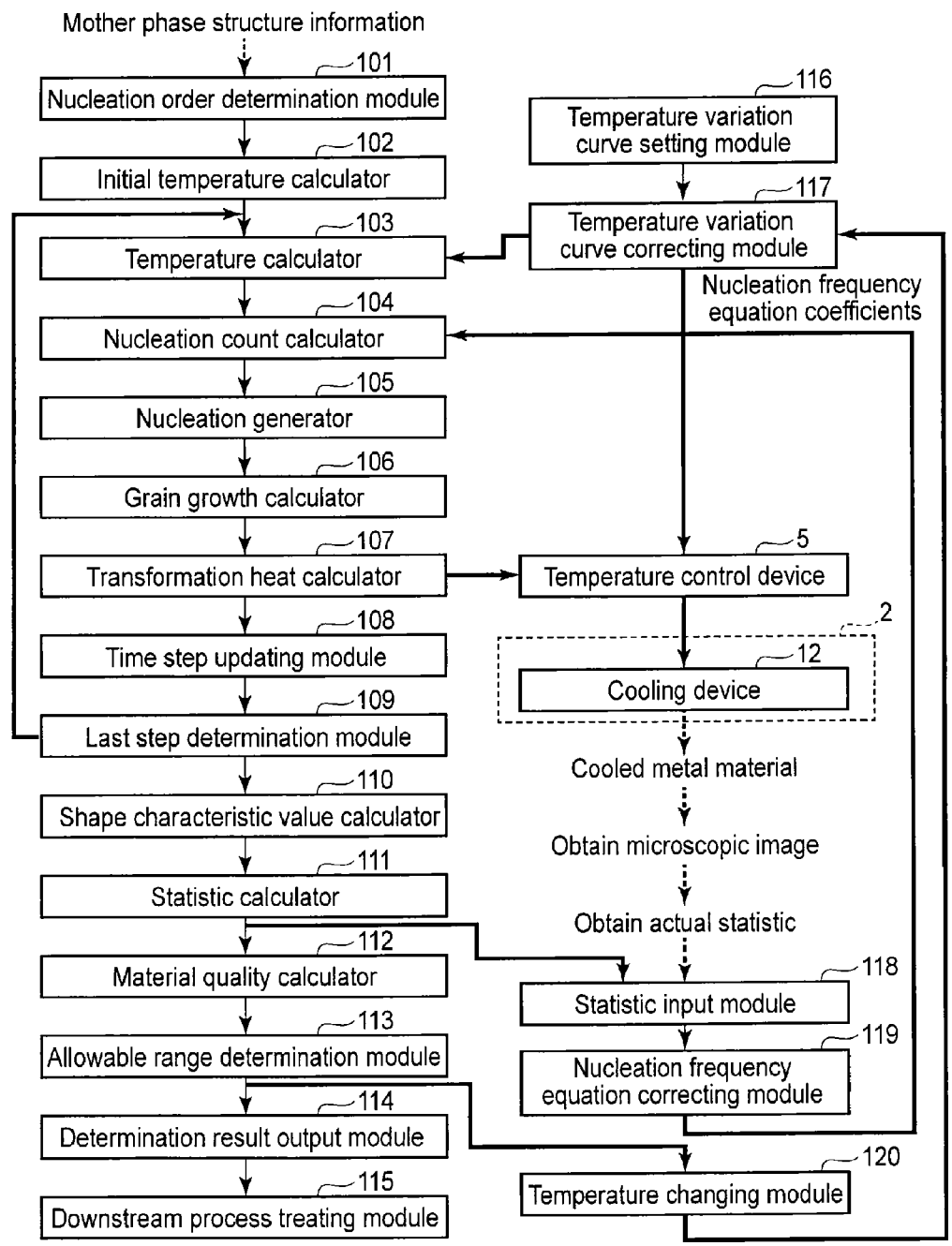
F I G. 1

FIG. 4

| | | | L4 | | L4 | | L3 | | |
|---|---|---|---|---|---|---|---|---|---|
| 0 | 0 | 4 | 0 | 0 | 0 | 0 | 3 | 0 | |
| 0 | 0 | 0 | 4 | 0 | 0 | 3 | 0 | 0 | |
| 0 | 0 | 0 | 5 | 4 | 4 | 5 | 0 | 0 | |
| 0 | 0 | 0 | 3 | 0 | 0 | 2 | 0 | 0 | |
| 0 | 0 | 3 | 0 | 0 | 0 | 2 | 0 | 0 | L2 |
| 1 | 1 | 5 | 0 | 0 | 0 | 0 | 5 | 4 | |
| 0 | 0 | 3 | 0 | 0 | 0 | 3 | 0 | 0 | L4 |
| 0 | 0 | 0 | 3 | 0 | 0 | 3 | 0 | 0 | L3 |
| 0 | 0 | 0 | 5 | 2 | 2 | 5 | 0 | 0 | |
| 0 | 0 | 0 | 4 | 0 | 0 | 3 | 0 | 0 | |

FIG. 5

| | L4 | | L4 | | L3 | | | |
|---|---|---|---|---|---|---|---|---|
| 28 | 68 | 12 | 35 | 75 | 47 | 74 | 15 | 64 |
| 44 | 52 | 85 | 10 | 36 | 62 | 19 | 76 | 48 |
| 39 | 59 | 69 | 04 | 08 | 11 | 03 | 34 | 57 |
| 67 | 38 | 83 | 14 | 31 | 87 | 22 | 41 | 84 |
| 80 | 79 | 18 | 55 | 61 | 56 | 25 | 89 | 77 |
| 26 | 27 | 06 | 51 | 43 | 37 | 29 | 02 | 07 |
| 66 | 90 | 21 | 88 | 30 | 73 | 17 | 82 | 49 |
| 53 | 46 | 86 | 13 | 65 | 78 | 20 | 42 | 58 |
| 40 | 32 | 70 | 04 | 24 | 23 | 05 | 50 | 33 |
| 45 | 60 | 54 | 09 | 81 | 71 | 16 | 63 | 72 |

MATERIAL STRUCTURE PREDICTION APPARATUS, PRODUCT MANUFACTURING METHOD AND MATERIAL STRUCTURE PREDICTION METHOD

CROSS REFERENCE TO RELATED APPLICATIONS

This application is a Continuation Application of PCT Application No. PCT/JP2012/072234, filed Aug. 31, 2012, the entire contents of which are incorporated herein by reference.

BACKGROUND OF THE INVENTION

1. Field of the Invention

The present invention relates generally to a material structure prediction apparatus capable of predicting the structure of a material that exhibits phase transformation due to variation in temperature, a product manufacturing method and a material structure prediction method.

2. Description of the Related Art

In recent years, there has been a demand to improve the quality of materials used for industrial products in view of environmental protection and energy saving. Further, it is known that such material features as tensile strength, yield stress, expansion, etc., are closely associated with material structure at the microscopic level. In view of this, the material feature of a product has come to be created by operating a condition after hot processing or a cooling condition after the hot processing, thereby altering temperature change curve used as an index for a change in temperature applied to materials.

Yet further, when a material obtained after cooling and polishing is observed using an electron back-scattering diffraction (EBSD) device as an application apparatus of a scanning type electron microscope, the crystal orientation of each crystal grain in a precipitated phase (new phase) can be obtained. A definite relationship exists between the crystal orientation of a mother phase and that of the precipitated phase. It is known that the crystal orientation and grain boundary of the mother phase can be reconstructed using the definite relationship (see non patent document 1). Also, researches have been conducted in association with a nucleation rate and a growth rate used for formulation of progress of diffusion transformation during cooling (see non patent document 2).

As a temperature control apparatus, an apparatus is disclosed in which the quantity of heat generated when a rolled material is subjected to phase transformation is predicted using a phase transformation heat generation model, and a winding temperature is controlled to coincide with a predetermined temperature target value with the transformation heat quantity compensated for (see patent document 1).

To establish appropriate manufacturing conditions for acquiring desired material properties, it is necessary to repeat test production. However, the process of repeating test production involves much cost and labor. In the field of iron and steel materials, a structure material-quality prediction technique for predicting the structure and quality of a material as a product have been developed for a hot rolling process. The structure material-quality prediction technique is used to properly control a manufacturing condition, such as a temperature variation curve, in order to obtain desired material properties.

In existing structure material-quality prediction models, it is assumed that the material structure is uniform. Accordingly, no consideration is given to differences or variations in crystal grain size and shape in the material structure. Actually, however, each crystal grain differs in size and shape, and variation therein may sometimes be great, depending upon manufacturing conditions. These factors may well change the quality of the material.

Further, solid-phase transformation in a cooling process of a material from a hot state includes two phenomena, i.e., (i) crystal nucleation and (ii) growth of created crystal grains. Regarding the latter (crystal grain growth), an analysis method called a multi-phase-field (MPF) method is known. For instance, in single-crystal growth, a simulation method is disclosed in which a change in grain shape due to grain growth is calculated using the multi-phase-field method (see patent document 2). Regarding the former (nucleation), however, merely a simple consideration that, for example, initial nucleation positions are manually imparted at the start of calculation is given in the conventional multi-phase-field method, irrespective of the fact that the position and time of an actual nucleation are determined from the structure of a mother structure and temperature variation. Further, although patent document 2 considers nucleation caused by distortion energy due to dislocation in a single crystal, the application of the method disclosed therein to a polycrystal metal has limitations, because, for example, it is known that in a polycrystal metal such as steel, nucleation may easily occur in the vicinity of the grain boundary of a mother phase structure.

The conventional multi-phase-field method is insufficient in quantitative prediction accuracy since it does not sufficiently consider nucleation behaviors, although it can obtain a qualitative tendency of variation due to grain growth for difference in crystal grain size and shape and these variations in a material structure. Consequently, it is difficult to apply the disclosed analysis method to a case where quantitative evaluation, such as prediction of material quality after cooling, is needed.

As described above, by the conventional multi-phase-field method, it is difficult for use in the quantitative evaluation of, for example, material quality to predict the structure of a material that exhibits phase transformation as a result of temperature variation.

PRIOR ART DOCUMENTS

Patent Documents

Patent Document 1: Jpn. Pat. Appln. KOKAI Publication No. 2005-297015
Patent Document 2: Jpn. Pat. Appln. KOKAI Publication No. 2007-091543

Non Patent Documents

Non Patent Document 1: Toshiharu Morimoto and four others, "Development of Variant Analysis Program by Using EBSD Data," "Iron and Steel," published by The Iron and Steel Institute of Japan, 2007, Vol. 93, No. 9, pp. 27-35
Non Patent Document 2: Masayoshi Suehiro and four others, "A Kinetic Model for Phase Transformations of Low Carbon Steels during Continuous Cooling," "Iron and steel," published by The Iron and Steel Institute of Japan, 1987, Vol. 73, No. 8, pp. 110-117

BRIEF SUMMARY OF THE INVENTION

It is an object of the invention to provide a material structure prediction apparatus capable of quantitatively predicting the structure of a material that exhibits phase transformation in accordance with a temperature variation, a product producing method, and a material structure predicting method.

In accordance with an aspect of the invention, there is provided a material structure prediction apparatus predicting a structure of a material that exhibits phase transformation from a mother phase to a precipitated phase in accordance with a temperature variation. The material structure prediction apparatus comprises a temperature calculator configured to calculate temperatures at calculation points in a calculation target region of the material, based on a temperature condition for applying the temperature variation to the material; a nucleation count calculator configured to calculate a nucleation count in the calculation target region, based on the temperatures at the calculation points calculated by the temperature calculator; a precipitated phase generation point determining module configured to determine, from the calculation points, a precipitated phase generation point where a nucleus of the precipitated phase is generated, based on the nucleation count calculated by the nucleation count calculator; a grain growth calculator configured to calculate a grain growth of the precipitated phase at the precipitated phase generation point determined by the precipitated phase generation point determining module; and a material structure prediction module configured to predict the structure of the material, based on the grain growth of the precipitated phase calculated by the grain growth calculator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing the configuration of a material structure prediction apparatus according to an embodiment of the invention;

FIG. 4 is a schematic view showing a metal material sample in which calculation points are classified into different levels by a nucleation order determination module according to the embodiment; and FIG. 5 is a schematic view showing a metal material sample in which the order of nucleation of the calculation points is determined by the nucleation order determination module of the embodiment.

DETAILED DESCRIPTION OF THE INVENTION

Figure 2:
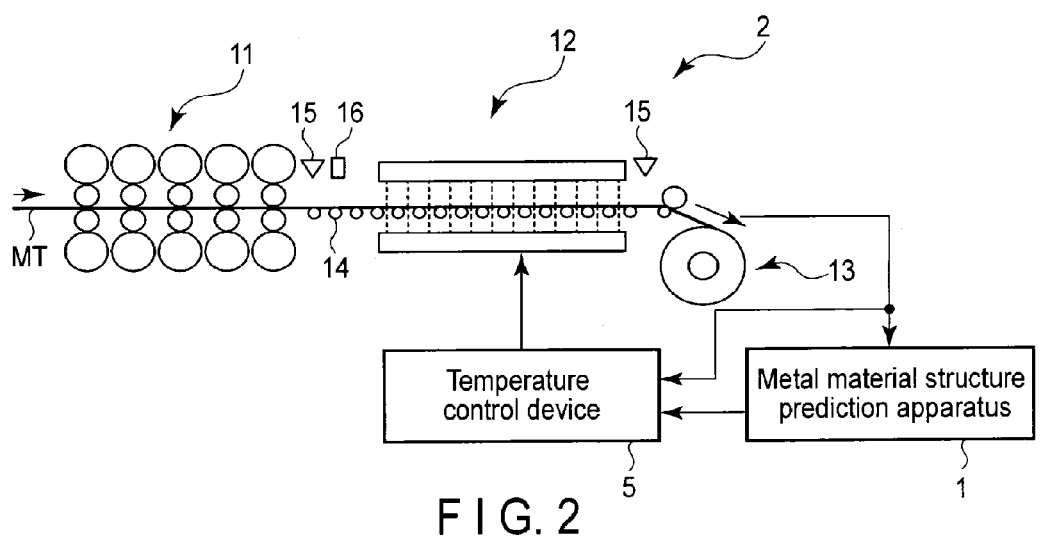
FIG. 2 is a view showing the structure of a hot strip mill line to which the material structure prediction apparatus of the embodiment is applied.

An embodiment of the present invention will be described below with reference to the accompanying drawings.

Embodiment

FIG. 1 is a block diagram showing the configuration of a material structure prediction apparatus 1 according to an embodiment of the invention. In the drawings, like reference numbers denote like portions, the detailed explanations thereof will be omitted, and different portions will be mainly described.

Firstly, a description will be given of a general metal material processing line to which the material structure prediction apparatus 1 is applied.

In the metal material processing line, at least heating or cooling is performed on a metal material.

An induction heating device, a gas heating device, or the like, is used as a heating device. A water cooling device, an oil cooling device, a forced air cooling device, or the like, may be used as a cooling device. A plurality of heating devices and/or cooling devices may be employed. Further, the order of arrangement of the heating and cooling devices can be set arbitrarily.

A description will be given of a structure in which the material structure prediction apparatus 1 is applied to a hot strip mill line 2 as an example of the metal material processing line. Further, in the description, a case where a metal material MT is cooled is mainly described. However, the same can be said of a case where the metal material MT is heated.

FIG. 2 shows the configuration of the hot strip mill line 2 to which the material structure prediction apparatus 1 of the embodiment is applied. More specifically, FIG. 2 shows a runout table incorporated in the hot strip mill line 2 and its vicinity.

The hot strip mill line 2 is equipment for manufacturing a product of a desired material from the metal material MT. The hot strip mill line 2 includes a finish roller 11, a water cooling device 12, a winding machine 13, conveyance rollers 14, radiation thermometers 15 and an optical metal detector 16.

After rolled by the finish roller 11, the heated metal material MT is cooled by the water cooling device 12 while being conveyed by the conveyance rollers 14. The water cooling device 12 is, for example, a laminar water cooling device. The metal material MT cooled by the water cooling device 12 is wound up by the winding machine 13. Various data items on the metal material MT, obtained by the radiation thermometers 15 and the optical metal detector 16, are sent to a temperature control device 5.

The temperature control device 5 controls the cooling device 12 so as to make the temperature variation of the metal material MT coincide with a preset cooling curve (temperature variation curve) on the basis of temperatures measured by the radiation thermometers 15, and a predicted value of heat generation due to the phase transformation of the metal material MT and received from the material structure prediction apparatus 1.

The material structure prediction apparatus 1 is mainly formed of a computer. On the basis of various data items on the metal material MT, received from the hot strip mill line 2, the material structure prediction apparatus 1 computes for, for example, predicting the structure of the metal material MT and evaluating the quality of the metal material MT. The material structure prediction apparatus 1 sends the computation result to the temperature control device 5. The computation result includes data concerning the metal material MT, such as a predicted value of heat generation due to the phase transformation.

The material structure prediction apparatus 1 starts calculation for predicting the structure of the metal material MT and evaluating the quality of the same, for example, when the metal material MT has reached a predetermined position on the hot strip mill line 2, or when an instruction to start calculation is issued via the operation screen of the material structure prediction apparatus 1. The predetermined position is, for example, just below the radiation thermometers 15 provided at the upstream side of the water cooling device 12. The arrival of the metal material MT at the predetermined position is detected on the basis of, for example, a detection signal output by the optical metal detector 16 provided in a desired position on the line or an actual conveyance distance calculated from the number of rotations of the conveyance rollers 14 detected by a rotation meter dedicated thereto.

Figure 3:
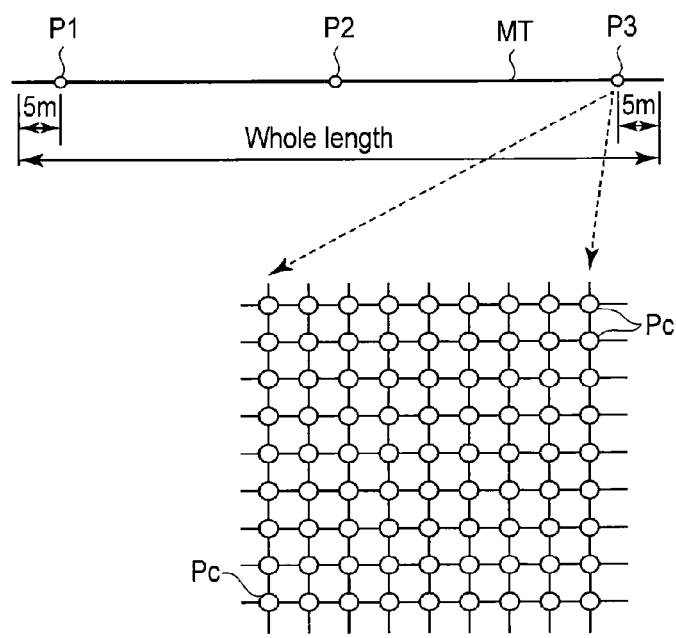
FIG. 3 is a schematic view showing the position of the calculation target region of a material in the hot strip mill line of the embodiment.

A calculation target region as a calculation target for predicting the structure of the metal material MT is predetermined. The calculation target region serves as a position that represents a processing condition, such as a temperature condition or cooling condition (heating condition), which influences the material structure. An arbitrary number of calculation target regions may be employed. However, it should be noted that too much calculation target regions inevitably increase the number of calculations. In the embodiment, three calculation target regions are employed for the metal material MT in the hot strip mill line 2 as shown in FIG. 3. Namely, position P1 5 m from the longitudinal front end of the metal material MT obtained after rolling, position P2 at the middle of the length of the rolled metal material MT, and position P3 5 m from the longitudinal rear end of the rolled metal material MT, are employed. Further, positions P1 to P3 are assumed to be at a quarter of the thickness of the rolled metal material MT from the upper surface thereof.

Further, if the calculation target regions are too small, the shape characteristic value of each crystal grain cannot accurately be measured. At the same time, if the calculation target regions have a predetermined size or more, the accuracy of the statistic of the shape characteristic values does not greatly vary. However, if the calculation target regions are too large, the number of calculations inevitably increases. In light of these, when the shape characteristic value of each crystal grain is evaluated, it is desirable to set the calculation target region to 5 to 5000 times the supposed crystal grain diameter of a precipitated phase.

Referring now to FIG. 3, a description will be given of the arrangement of calculation points Pc. The material structure prediction apparatus 1 arranges a large number of calculation points Pc in a mesh in each calculation target region. If the intervals of the calculation points Pc is too large, the shape characteristic value of each crystal grain cannot accurately be determined, while if the intervals is too small, the number of calculations increases. Accordingly, it is desirable to set the intervals of the calculation points Pc in each calculation target region to $1/500$ to $1/5$ of the supposed crystal grain diameter of a precipitated phase.

In order to hold data concerning each calculation point, the material structure prediction apparatus 1 secures a storage region for storing temperature calculation values, a nucleation order, and the concentration c of an element diffused in accordance with phase transformation (e.g., in the phase transformation of from austenite to ferrite, carbon), and a scalar quantity $\phi$.

The capacity for the storage region of the temperature calculation values, the nucleation order, and the concentration of the diffused element is (the number of calculation target regions)*(the size of each calculation target region)/(the interval of the calculation points).

The capacity for the storage region of the scalar quantity $\phi$ is (the total number of crystals)*(the number of the calculation target regions)/(the interval of the calculation points).

The scalar quantity $\phi$ represents the existing probability of the crystal grain in each calculation point. If the calculation point is within a crystal grain, the scalar quantity $\phi$ is 1. If the calculation point is outside the crystal grain, the scalar quantity $\phi$ is 0. If the calculation point is on a grain boundary, the scalar quantity $\phi$ is greater than 0 and smaller than 1.

FIG. 1 is a block diagram showing the configuration of the material structure prediction apparatus 1 according to the embodiment. The arrows in FIG. 1 mainly indicate the flow of information (or data).

The material structure prediction apparatus 1 includes a nucleation order determining module 101, an initial temperature calculator 102, a temperature calculator 103, a nucleation count calculator 104, a nucleation generator 105, a grain growth calculator 106, a transformation heat calculator 107, a time step updating module 108, a last step determination module 109, a shape characteristic value calculator 110, a statistic calculator 111, a material quality calculator 112, an allowable range determination module 113, a determination result output module 114, a downstream process treating module 115, a temperature variation curve setting module 116, a temperature variation curve correcting module 117, a statistic input module 118, a nucleation frequency equation correcting module 119 and a temperature changing module 120.

Firstly, an operator acquires information associated with the material structure of a mother phase (hereinafter referred to as "mother phase structure information") from a metal material sample. A description will now be given of a specific example of the method of acquiring the mother phase structure information.

The metal material sample is substantially equal in alloy components and an upstream process (temperature condition or process ratio) to the metal material MT whose structure is to be predicted. The operator rapidly cools the metal material sample with the mother phase kept (structure freezing), and polishes and etches the resultant structure. When the thus-processed metal material sample is observed using a microscope, an image in which the grain boundary of the mother phase is marked is obtained. If the metal material MT is iron or steel, the grain boundary of an austenite structure as the mother phase can be clearly observed by decomposing it in a picric solution. In general, in an image obtained after etching, the smaller the tilt angle of the grain boundary (the difference in crystal orientation between adjacent crystal grains), the thinner the grain boundary. The tilt angle can be detected by visually detecting the thickness and density of the grain boundary appearing in the image, or detecting the same using image analysis software.

Further, the crystal orientation of each crystal grain of the precipitated phase can be obtained from an image acquired by an electron back-scattering diffraction (EBSD) device, as an application apparatus of a scanning type electron microscope, after cooling and polishing the metal material sample. There is a constant relationship between the crystal orientation of the mother phase and that of the precipitated phase. Utilizing this relationship, the crystal orientation of the mother phase and the grain boundary can be reconstructed. Therefore, the tilt angle of the grain boundary can be detected from an image observed using the EBSD device.

Thus, the operator acquires mother phase structure information. The action of acquiring mother phase structure information from an image may be manually performed by the operator or be performed by the material structure prediction apparatus 1 via a program.

The nucleation order determining module 101 determines the nucleation order of each calculation point in each calculation target region of the metal material MT on the basis of the mother phase structure information. The nucleation order is indicative of the order of nucleation of precipitated phases from mother phases. In the embodiment, it is assumed that nucleation is made in an increasing nucleation order. In a polycrystalline metal, nucleation will easily occur in a portion in which a plurality of grain boundaries contact each other or the tilt angle of a grain boundary is large. Therefore, the nucleation order of the calculation points is determined so that a calculation point in the mentioned portion has a higher nucleation order.

Referring to FIGS. 4 and 5, a description will be given of a method of determining the order of nucleation by the nucleation order determining module 101. FIG. 4 is a schematic view showing a metal sample in which calculation points are classified into different levels by the nucleation order determination module 101. FIG. 5 is a schematic view showing a metal sample in which the order of nucleation of the calculation points is determined by the nucleation order determination module 101. Broken lines L1, L2, L3 and L4 in FIGS. 4 and 5 are indicative of the positions of the grain boundaries of the mother phases. It is assumed that each portion of the boundaries belongs to its closest calculation point.

The nucleation order determination module 101 determines the level of each of grain boundaries L1 to L4. Grain boundaries L1 to L4 are classified into four stages of levels 1 to 4 in accordance with their thicknesses and densities in an image of the metal material sample. Grain boundaries L1 to L4 are set such that the thicker and denser the grain boundary in the image, the higher the priority level of nucleation. The criterion for determining the thickness or density may be a predetermined absolute one, or be a relative one used to rank each grain boundary among all grain boundaries. In the embodiment, grain boundaries L1 to L4 are classified into levels, such as level 4 corresponding to a thick and dense ground boundary, level 3 corresponding to a relatively thick and dense ground boundary, level 2 corresponding to a normal grain boundary, and level 1 corresponding to a slim and thin grain boundary.

Subsequently, on the basis of the classified grain boundaries L1 to L4, calculation points are classified into different levels. In FIG. 4, the numerical values in respective squares (calculation points) indicate levels in the calculation points. The calculation points are classified as described below.

A calculation point in which grain boundary L4 of level 4 passes is set to level 4, a calculation point in which grain boundary L3 of level 3 passes is set to level 3, a calculation point in which grain boundary L2 of level 2 passes is set to level 2, and a calculation point in which grain boundary L1 of level 1 passes is set to level 1. A calculation point in which no grain boundary passes is set to level 0 indicative of the lowest nucleation order. A calculation point in which a plurality of grain boundaries L1 to L4 contact each other (i.e., a calculation point corresponding to a triple junction) is set to level 5 indicative of the highest nucleation order.

After classifying the calculation points, the nucleation order determining module 101 determines the order of nucleation of the calculation points. In FIG. 5, the numerical values in respective squares indicate the order of nucleation in the respective calculation points. The order of nucleation of each calculation point is determined as follows.

The nucleation order determining module 101 sequentially assigns numbers indicative of the order of nucleation to calculation points, beginning with a calculation point of the highest level. Accordingly, the smallest numbers are assigned to calculation points of level 5. Namely, nucleation is made earlier in these calculation points. Further, the largest numbers are assigned to calculation points of level 0. Yet further, for a plurality of calculation points of the same level, the order of nucleation is determined using random numbers, in order to avoid biased selection that is not intended by the operator or to avoid influence of a scanning order by image analysis software.

The initial temperature calculator 102 calculates an initial temperature for each calculation point in each calculation target region of the metal material MT. The initial temperature calculator 102 calculates the initial temperature on the basis of the measured values of the radiation thermometers 15. For calculation of the initial temperatures, values measured by a contact type thermometer or predicted values based on, for example, actual values in the upstream process may be used. The initial temperature calculator 102 may correct the calculated initial temperatures. For instance, the initial temperature calculator 102 corrects the calculated initial temperature in consideration of heat radiation from the surface of the metal material MT, convection of air, heat conduction in the interior of the material, etc., when the temperature measuring position for the metal material MT is away from the calculation target region, or when a certain time has elapsed after the measurement of the radiation thermometers 15. If the size of the calculation target region is sufficiently small relative to the slope of temperature, and temperature differences among a plurality of calculation points in the same calculation target region can be almost ignored, the same initial temperature may be set for all calculation points in the calculation target region. This way of initial temperature setting will cause only a restrictive reduction of calculation accuracy. Therefore, practically, it is sufficient if the initial temperature setting may be performed in consideration of the calculation accuracy reduction.

In the material structure prediction apparatus 1, after the calculations by the nucleation order determining module 101 and the initial temperature calculator 102, calculations by the temperature calculator 103, the nucleation count calculator 104, the nucleation generator 105, the grain growth calculator 106, the transformation heat calculator 107, the time step updating module 108 and the last step determination module 109 are performed in every time step. The material structure prediction apparatus 1 performs a series of calculations in each time step from start to end of cooling (or heating) of the metal material MT.

The temperature calculator 103 calculates the temperature of each calculation point in each calculation target region of the metal material MT in every time step. Before actually starting cooling (or heating) of the metal material MT, the temperature calculator 103 calculates temperatures for respective calculation points, using a target temperature variation curve. While the metal material MT is actually being cooled (or heated), the temperature calculator 103 calculates the temperature of each calculation point, using an actual temperature variation curve obtained up to a current calculation time, and the target temperature variation curve after the current calculation time. After actually cooling (or heating) the metal material MT, the temperature calculator 103 calculates the temperature of each calculation point using an actual temperature variation curve. For instance, the actual temperature variation curve is obtained from a temperature model utilizing a difference method on the basis of actual values, such as the flow volume of cooling water or the current of an induction heating device.

The nucleation count calculator 104 calculates a nucleation count $\Delta N\alpha$ in a calculation target region on the basis of a free-energy difference between a mother phase and a precipitated phase, and a diffusion coefficient. Firstly, the nucleation count calculator 104 calculates the nucleation frequency I of the precipitated phase from the mother phase. The nucleation frequency I is given by, for example, the following equation:

$$I = k_1 \cdot T^{-\frac{1}{2}} \cdot D_\gamma \cdot \exp\left(-\frac{k_2}{R \cdot T \cdot \Delta G_v^2}\right) \qquad \text{Equation (1)}$$

where R is a gas constant, T is an absolute temperature, and $D\gamma$ is the diffusion coefficient of an element diffusing in the mother phase in accordance with phase transformation and is a function of the concentration of the element and the temperature. Further, $\Delta Gv$ is a free-energy difference between the mother phase and the precipitated phase, and results from a thermodynamic database, k1 is a coefficient depending upon interfacial energy and dislocation density, and k2 is a coefficient depending upon activation energy.

The nucleation count calculator 104 calculates the nucleation count $\Delta N\alpha$ in the calculation target region in a certain time step, utilizing the calculated nucleation frequency I, using the following equations. Since the count $\Delta N\alpha$ is an integer, the decimal fraction part of the calculation result is stored as a residue "res". The stored residue "res" is added in a subsequent time step.

$$\Delta N_\alpha = \text{TRUNC}(I \cdot V_\gamma \cdot \Delta t + \text{res}) \qquad \text{Equation (2)}$$

$$\text{res} = (I \cdot V_\gamma \cdot \Delta t + \text{res}) - \Delta N_\alpha \qquad \text{Equation (3)}$$

where $\Delta t$ is a time increment, TRUNC is a function for truncating the decimal fraction part, and $V\gamma$ is the volume (area in the case of two-dimensional calculation) of a non-transformed part in the calculation target region. Whether or not a part is the non-transformed part is determined depending upon whether or not scalar quantity $\phi i$ in each calculation point is 0 in association with all crystal grains (i=1 to n).

The nucleation generator 105 generates $\Delta N\alpha$ nuclei for new precipitated phases in each time step in the calculation target region in accordance with the nucleation count $\Delta N\alpha$ calculated by the nucleation count calculator 104. Firstly, the nucleation generator 105 searches for calculation points beginning with a calculation point of the highest nucleation order. The nucleation generator 105 confirms whether the searched calculation point is not included in a precipitated phase. To confirm that the calculation point is not included in precipitated phases, it is sufficient if the fact that scalar quantity $\phi i$ in the calculation point is 0 in association with all crystal grains (i=1 to n) is confirmed. If the searched calculation point is already included in a crystal grain of another precipitated phase, a calculation point of the next highest nucleation order is searched for. By iterating this processing, the nucleation generator 105 determines a calculation point that is not included in the precipitated phases. The nucleation generator 105 generates a new crystal nucleus in the determined calculation point.

More specifically, the following computing is performed. The nucleation generator 105 increments by one the total number n of crystal grains, and newly assigns a storage region to scalar quantity $\phi n$ associated with the incremented crystal grain. The nucleation generator 105 sets, to 1, scalar quantity $\phi n$ associated with a newly produced crystal grain in a calculation point where a crystal nucleus is produced, and sets, to 0, scalar quantity $\phi n$ associated with the newly produced crystal grain in the other calculation points.

The grain growth calculator 106 calculates movement of the interface of the precipitated phase due to the grain growth thereof, using the multi-phase-field method. More specifically, the grain growth calculator 106 updates scalar quantity $\phi i$ in all calculation points using the following equations:

$$\phi_i(t + \Delta t) = \phi_i(t) + \left(\frac{\partial \phi_i}{\partial t}\right) \cdot \Delta t \qquad \text{Equation (4)}$$

$$\frac{\partial \phi_i}{\partial t} = \sum_{j=1}^{n}\left[\frac{\mu_{ij}}{n} \cdot \sum_{k=1}^{n}\left\{\begin{array}{l}(\sigma_{jk} - \sigma_{ik}) \cdot \nabla^2 \phi_k + \\ (\sigma_{jk} - \sigma_{ik}) \cdot \frac{\pi^2}{\eta^2}\phi_k\end{array}\right\} + \frac{2\pi}{\eta} \cdot \sqrt{\phi_i\phi_j} \cdot (G_j - G_i)\right] \qquad \text{Equation (5)}$$

where n is the total number of crystal grains, and i, j and k are numbers assigned to the crystal grains. Crystal grain number 1 is indicative of the mother phase. $\eta$ is a calculation interval. Gi and Gj are the free energy values of crystal grains obtained utilizing values in the thermodynamic database. $\mu$ is the mobility of an interface. $\sigma$ is interfacial energy. $\mu$ and $\sigma$ are constants resulting from the alloy composition of the material.

Further, the grain growth calculator 106 updates the concentration c of an element that will diffuse in accordance with phase transformation, using the following diffusion equations:

$$c_i(t + \Delta t) = c_i(t) + \left(\frac{\partial c_i}{\partial t}\right) \cdot \Delta t \qquad \text{Equation (6)}$$

$$\frac{\partial c_i}{\partial t} = \nabla\{\phi_\alpha D_\alpha \nabla c_\alpha + \phi_\gamma D_\gamma \nabla c_\gamma\} \qquad \text{Equation (7)}$$

where $\gamma$ is the mother phase, and $\alpha$ is the precipitated phase. $D\alpha$ is the diffusion coefficient of the precipitated phase of the element that will diffuse in accordance with phase transformation. $\nabla$ is a vector differentiation operator.

The transformation heat calculator 107 calculates the enthalpy $H\alpha$ of the mother phase and the enthalpy $H\gamma$ of the precipitated phase at temperature T, utilizing the free energy of the crystal grain, using the following equations based on Gibbs-Helmholtz equations:

$$H_\alpha = -T^2 \cdot \frac{\partial}{\partial T}\left(\frac{G_\alpha}{T}\right) \qquad \text{Equation (8)}$$

$$H_\gamma = -T^2 \cdot \frac{\partial}{\partial T}\left(\frac{G_\gamma}{T}\right) \qquad \text{Equation (9)}$$

Subsequently, the transformation heat calculator 107 calculates a transformation heat quantity Q per unit weight on the basis of a calculation result indicative of the movement of a precipitated phase interface due to grain growth, using the following equation:

$$Q = \sum_{i=1}^{n} \left\{ \frac{1}{M} \cdot w_i \cdot \phi_i \cdot (H_\gamma - H_\alpha) \right\} \quad \text{Equation (10)}$$

where wi is the weight of the portion occupied by a calculation point i, and M is molar mass.

The transformation heat calculator 107 transmits, to the temperature control device 5, data indicative of the calculated transformation heat quantity Q per unit weight. On the basis of the transformation heat quantity Q calculated by the transformation heat calculator 107, the temperature control device 5 controls the water cooling device 12 of the hot strip mill line 2 to make it cool the metal material MT in accordance with a target temperature variation curve.

After the transformation heat calculator 107 finishes calculation processing, the time step updating module 108 updates the time step. The increase in the time step due to updating is made to fall within a range in which the movement of the interface calculated by the above diffusion equations does not exceed the interval between calculation points.

The last step determination module 109 determines whether a finish condition is satisfied. If the finish condition is not satisfied, the material structure prediction apparatus 1 returns to calculation processing by the temperature calculator 103, where a series of calculation processing described above is iterated. As a result, variation in material structure in a calculation target region of the metal material MT is simulated.

If the last step determination module 109 has determined that the finish condition is satisfied, the material structure prediction apparatus 1 executes subsequent computing. Computing, which will now be described, may be included in the above-described series of computing.

The shape characteristic value calculator 110 calculates various shape characteristic values for each crystal grain on the basis of the scalar quantity ϕ. The shape characteristic values include a grain area, an area ratio, a grain size, an equivalent circle diameter, the major axis length of an equivalent ellipsoid, the minor axis length of the equivalent ellipsoid, the major-axis to minor-axis ratio of the equivalent ellipsoid, a boundary length, a roundness, a grain volume, a volume ratio, an equivalent sphere diameter, the major axis length of an equivalent ellipsoidal body, the minor axis length of the equivalent ellipsoidal body, the major-axis to minor-axis ratio of the equivalent ellipsoidal body, a surface area, etc. The shape characteristic value calculator 110 integrates, for example, scalar quantities ϕi of crystal grains of numbers i included in the entire calculation target region and thereby calculates grain area Ai (in the case of two-dimensional calculation) or grain volume Vi (in the case of three-dimensional calculation), using the following equations:

$$A_i = \sum_i \phi_i \quad \text{Equation (11)}$$

$$V_i = \sum_i \phi_i \quad \text{Equation (12)}$$

The shape characteristic value calculator 110 calculates equivalent circle diameter di on the basis of the above-calculated grain surface Ai or grain volume Vi, using the following equations:

$$d_i = \sqrt{\frac{4}{\pi} \cdot A_i} \quad \text{Equation (13)}$$

$$d_i = \sqrt[3]{\frac{6}{\pi} \cdot V_i} \quad \text{Equation (14)}$$

The statistic calculator 111 calculates a statistic of the shape characteristic values of the crystal grains calculated by the shape characteristic value calculator 110. The statistic is, for example, the grade of the shape characteristic value, a maximum value, a minimum value, a variance, an average value, a weighted average based on a grain area, a weighted average based on a grain volume, a standard deviation, a gamma distribution coefficient, a Weibull distribution coefficient, an average grain diameter based on an intercept method, an average grain diameter based on a comparison method, a grain size number based on the American Society for Testing and Materials (ASTM) standards, etc.

In the two-dimensional calculation, the statistic calculator 111 calculates a weighted average grain diameter based on the grain area, using the following equation:

$$\bar{d} = \frac{\sum_{i=1}^{n} (d_i \cdot A_i)}{\sum_{i=1}^{n} A_i} \quad \text{Equation (15)}$$

where n is the number of crystal grains.

In the three-dimensional calculation, the statistic calculator 111 calculates a weighted average grain diameter based on the grain volume, using the following equation:

$$\bar{d} = \frac{\sum_{i=1}^{n} (d_i \cdot V_i)}{\sum_{i=1}^{n} V_i} \quad \text{Equation (16)}$$

In the two-dimensional calculation, the statistic calculator 111 calculates a weighted average grain diameter standard deviation based on the grain area, using the following equation:

$$\sigma_d = \sqrt{\frac{\sum_{i=1}^{n} \left\{ (d_i - \bar{d})^2 \cdot A_i \right\}}{\sum_{i=1}^{n} A_i}} \quad \text{Equation (17)}$$

In the three-dimensional calculation, the statistic calculator 111 calculates a weighted average grain diameter standard deviation based on the grain volume, using the following equation:

$$\sigma_d = \sqrt{\frac{\sum_{i=1}^{n}\{(d_i - \bar{d})^2 \cdot V_i\}}{\sum_{i=1}^{n} V_i}} \quad \text{Equation (18)}$$

The material quality calculator 112 calculates the quality of the metal material MT on the basis of the statistic of the shape characteristic values calculated by the statistic calculator 111. The calculated material quality is the predicted quality of the metal material MT after cooling (or heating). The material quality is, for example, yield stress (YS), tensile strength (TS), elongation (EL), hardness, toughness, hole expandability, magnetism, etc.

For instance, the material quality calculator 112 calculates the yield stress YS on the basis of the Hall-Petch rule, using the following equation:

$$Y_S = \frac{k}{\sqrt{d}} \quad \text{Equation (19)}$$

where k is a constant predetermined by, for example, experiments.

The allowable range determination module 113 determines whether the quality of the metal material MT calculated by the material quality calculator 112 falls within an allowable range. The allowable range determination module 113 outputs the determination result to the determination result output module 114.

The determination result output module 114 outputs the determination result of the allowable range determination module 113 to, for example, a display screen or a storage medium. If the quality of the metal material MT falls outside the allowable range, the determination result output module 114 performs, for example, processing as below. The determination result output module 114 outputs, to the display screen or storage medium, data indicative of the position, in the metal material MT, of a calculation target region that falls outside the allowable range, or the position, in the calculation target region, of a crystal grain that falls outside the allowable range. To inform the operator that the quality of the metal material MT falls outside the allowable range, the determination result output module 114 outputs a warning signal (a display on the screen or an alarm). The determination result output module 114 outputs information needed for the downstream process treating module 115 in order to process, in the downstream process, the portion of the metal material MT falling outside the allowable range.

The downstream process treating module 115 compute for processing, in the downstream process, the portion of the metal material MT determined to fall outside the allowable range by the allowable range determination module 113. In the case of, for example, the hot strip mill line, the downstream process is, for example, a cutting, welding, cold rolling, acid washing, leveling, skin pass, etc. The downstream process treating module 115 tracks a calculation target region determined to fall outside the allowable range of the metal material MT, using an optical metal detector 16 provided on the hot strip mill line 2 or a rotation meter incorporated in the conveyance roller 14. To enable the portion of the metal material MT falling outside the allowable range to be processed, the downstream process treating module 115 transmits, for example, track information to a downstream process for processing the mentioned portion. For instance, in the case where the downstream process is a cutting process using a cutting device, the cutting device cuts out the portion of the metal material MT falling outside the allowable range when the portion has reached the cutting device. Thus, the portion whose material quality falls outside the allowable range is removed from the metal material MT.

A description will now be given of a method of changing a temperature set for the metal material MT, when the allowable range determination module 113 has determined that the quality of the metal material MT falls outside the allowable range.

When the allowable range determination module 113 has determined that the quality of the metal material MT falls outside the allowable range, the temperature changing module 120 performs calculation for correcting a temperature variation curve or an input/output heat quantity in the calculation target region determined to fall outside the allowable range, so that the statistic processing result associated with the shape characteristic values of crystal grains in the precipitated phases calculated by the statistic calculator 111 will fall within the allowable range.

For instance, if the grain diameter standard deviation calculated by the statistic calculator 111 falls outside an allowable range, the temperature changing module 120 changes a temperature Tp at a certain nodal point p obtained when a temperature variation curve used for controlling the temperature control device 5 is expressed by a broken line, using the following expression:

$$T_p \leftarrow T_p - \frac{\sigma_d - \sigma_{dAIM}}{\left(\frac{\partial \sigma_d}{\partial T_p}\right)} \quad \text{Expression (20)}$$

where σdAIM is a target value of the grain diameter standard deviation. For instance, σdAIM is the median value of the allowable range.

The temperature changing module 120 performs trial calculation of two values σd(Tp+ΔT) and σd(Tp−ΔT) of the grain diameter standard deviation obtained when a fine value ±Δ is added to the temperature Tp. On the basis of the result of the trial calculation, the temperature changing module 120 calculates an influence coefficient, using the following equation:

$$\left(\frac{\partial \sigma_d}{\partial T_p}\right) = \frac{\sigma_d(T_p + \Delta T) - \sigma_d(T_p - \Delta T)}{2 \cdot \Delta T} \quad \text{Equation (21)}$$

where $\left(\frac{\partial \sigma_d}{\partial T_p}\right)$ is an influence coefficient If the temperature Tp exceeds an upper limit Tpmax for operation, the temperature changing module 120 sets the temperature Tp to the upper limit Tpmax. If the temperature Tp is below a lower limit Tpmin for operation, the temperature changing module 120 sets the temperature Tp to the lower limit Tpmin. The temperature changing module 120 outputs the calculated temperature Tp of the nodal point p to the temperature variation curve correcting module 117.

The temperature variation curve correcting module 117 corrects the temperature of the nodal point p of the temperature variation curve set in the temperature variation curve setting module 116, to the temperature Tp calculated by the temperature changing module 120. As a result, the temperature variation curve is corrected so that the grain diameter standard deviation falls within an allowable range.

A description will be given of a method of correcting the coefficients of the nucleation frequency equation.

Firstly, the actual value of a statistic of the shape characteristic values of the metal material MT after completion of cooling (or heating).

The operator obtains a microscopic or an electron microscopic picture of the metal material MT after the completion of cooling (or heating). The operator subjects the obtained picture to image analysis to thereby obtain the actual value of the statistic of the shape characteristic values. For instance, if a ferrite structure obtained after polishing an iron and steel specimen is decomposed by nital solution, the grain boundaries of the resultant ferrite crystal grains can be clearly observed. The operator photographs the thus-treated iron and steel specimen using an optical microscope or a scanning electron microscope. The thus-obtained image is input to an image processing apparatus, where it is subjected to brightness adjustment and then to binarization based on an appropriate threshold associated with contrasting density, thereby extracting grain boundaries. After that, the operator counts the number of the pixels of each crystal grain, converts each counted number into an area, and adds up the resultant conversion values. As a result, a statistic, such as an average grain diameter or a grain diameter standard deviation, can be obtained. Alternatively, the statistic, such as the average grain diameter or the grain diameter standard, deviation, can be obtained using the EBSD apparatus. Yet alternatively, the operator iteratively may bounce longitudinal ultrasound against the metal material MT. In this case, the statistic, such as the average grain diameter, can be obtained from the attenuation characteristic of a reflected detection wave.

The operator inputs the actual value of the thus-obtained statistic of the shape characteristic values to the statistic input module 118 of the material structure prediction apparatus 1. The actual value may be input to the material structure prediction apparatus 1 via an image processing apparatus or a storage medium.

The statistic input module 118 receives a predicted statistic calculated by the statistic calculator 111 and the actual value of the measured statistic. The statistic input module 118 outputs the predicted value and actual value of the statistic to the nucleation frequency equation correcting module 119.

The nucleation frequency equation correcting module 119 corrects the coefficients of the nucleation frequency equation as described below on the basis of the predicted statistic and the actual statistic.

The nucleation frequency equation correcting module 119 calculates the deviation between the predicted value σd of the statistic and the actual value σdACT of the statistic. The nucleation frequency equation correcting module 119 corrects coefficients k1 and k2 in the nucleation frequency equation shown in the equation (1) used by the nucleation count calculator 104 to reduce the deviation.

Coefficient k1 is corrected using the following expression:

$$k_1 \leftarrow k_1 - \frac{\sigma_d - \sigma_{dACT}}{\left(\frac{\partial \sigma_d}{\partial k_1}\right)} \quad \text{Expression (22)}$$

where $\left(\frac{\partial \sigma_d}{\partial k_1}\right)$ is an influence coefficient.

The nucleation frequency equation correcting module 119 performs a trial calculation of two values σd(k1+Δk1) and σd(k1−Δk1) obtained when fine values ±Δk1 are added to coefficient k1. On the basis of the trial calculation results, the nucleation frequency equation correcting module 119 calculates an influence coefficient using the following equation:

$$\left(\frac{\partial \sigma_d}{\partial k_1}\right) = \frac{\sigma_d(k_1 + \Delta k_1) - \sigma_d(k_1 - \Delta k_1)}{2 \cdot \Delta k_1} \quad \text{Equation (23)}$$

If coefficient k1 exceeds an upper limit k1max for operation, the nucleation frequency equation correcting module 119 sets coefficient k1 to the upper limit k1max. If coefficient k1 is lower than a lower limit k1min for operation, the nucleation frequency equation correcting module 119 sets coefficient k1 to the lower limit k1min.

The thus-corrected coefficients k1 and k2 may be stored for each layers in accordance with the alloy composition of the material. For instance, in the case of iron and steel materials, it is classified by layer such as ultralow carbon steel, low carbon steel, medium carbon steel, high carbon steel, niobium steel and chrome steel may be discriminated in accordance with carbon content, niobium content, chrome content, etc. By virtue of this structure, the influence of the difference due to the alloy composition can be corrected.

The degree of variation in crystal grain diameter is strongly correlated with the behavior of nucleation. For instance, a crystal grain whose nucleation occurred in an initial stage has a tendency to sufficiently grow into a large diameter grain. In view of this, for the calculation of the coefficients of the nucleation frequency equation, it is preferable to employ, as a shape characteristic value, the standard deviation of crystal grain diameters, the gamma distribution coefficient, the Weibull distribution coefficient, or a statistic associated with crystal grain distribution, such as the ASTM grain size number.

Although in the above, correction of coefficient k1 has been described, the same method can be applied to the correction of coefficient k2. Further, although equation (1) is used as the nucleation frequency equation, the coefficients of the nucleation frequency equation can be corrected by the same procedure as the above, even using another equation.

The present embodiment can provide the following operation and effect.

In the conventional multi-phase-field method, sufficient quantitative prediction accuracy cannot be obtained because in simulation of a cooling process (or heating process), an appropriate number of nuclei, from which solid-phase transformation will occur, cannot be produced at appropriate times.

In contrast, in the material structure prediction apparatus 1 of the embodiment, by performing calculation in association with the combination of the nucleation and grain growth of the metal material MT, an appropriate number of nuclei can be produced at appropriate times in appropriate positions near, for example, the grain boundaries of the mother phase structure, whereby the structure of the metal material MT that exhibits phase transformation in accordance with temperature variation can be quantitatively predicted.

Accordingly, the material structure prediction apparatus 1 can predict the quality of a material at high accuracy by predicting the material quality resulting from thermal process of the metal material MT (cooling, heating, isothermal process, etc.) on the basis of the quantitative prediction result of the metal material MT structure.

Further, since the material structure prediction apparatus 1 evaluates the prediction result associated with the quality of the metal material MT after the thermal process, it can reflect the evaluation result in a process of manufacturing a product. For instance, in a system (e.g., the hot strip mill line 2) of manufacturing the product, the quality of the metal material MT processed after the evaluation can be enhanced by collecting a plurality of evaluation results. Yet further, in the system of manufacturing the product, if the estimation result of the quality of the heated metal material MT falls outside an allowable range, the material quality of the product obtained by processing the metal material MT can be corrected within the allowable range by treating, in a downstream process, the portion of the metal material MT determined to fall outside the allowable range.

Moreover, the material structure prediction apparatus 1 calculates the quantity of heat generated during transformation on the basis of the calculation result concerning grain growth. On the basis of the transformation heat quantity calculated by the material structure prediction apparatus 1, the hot strip mill line 2 controls the temperature applied to the metal material MT, thereby realizing temperature control that reflects the behavior of the solid-phase transformation.

Further, the material structure prediction apparatus 1 corrects the coefficients in the nucleation frequency equation so that a predicted value calculated for the statistic concerning the shape characteristic values of crystal grains in a precipitated phase will be equal to the actual value of the statistic concerning the shape characteristic values of crystal grains in the precipitated phase obtained after heat treatment. However, nucleation is a probabilistic phenomenon and is not yet sufficiently theoretically clarified. Therefore, the nucleation frequency equation inevitably includes some errors. In view of this, the coefficients in the nucleation frequency equation are corrected on the basis of actual values. This enables the calculation accuracy of the nucleation behavior in the material structure prediction apparatus 1 to be enhanced. As a result, the prediction accuracy of the material structure prediction apparatus 1 for predicting the metal material MT structure is enhanced.

In the embodiment, the materials as prediction targets are not limited to the above-described ones. For instance, polycrystalline materials that exhibit phase transformation include a material, iron and steel materials (that contain, as dissolved substances, carbon, manganese, niobium, nickel, aluminum, nitrogen, etc.), magnetic materials (alloys or oxides of copper, iron, platinum, palladium, cobalt, chrome, nickel, neodymium, barium, bismuth, samarium, etc.), dielectric materials, functional materials represented by organic polymeric materials like block copolymers, such as polystyrene-polymethylmethacrylate. More specifically, in the magnetic materials, nucleation or phase separation will occur during thermal treatment, such as heating or cooling (including an isothermal process, annealing, aging treatment, etc.), whereby various microstructures are formed. Also in the dielectric and polymeric materials, various structure patterns are formed during thermal treatment, such as heating or cooling. In view of this, material structures produced as a result of phase transformation or phase separation during heat treatment of these materials may be quantitatively predicted using the same method as employed in the embodiment. For instance, the prediction method using the material structure prediction apparatus may be applied to a process of crystallizing organic materials.

In the embodiment, as mother and precipitated phases to predict, an arbitrary combination of phases may be selected. For instance, in the iron and steel materials, a material structure resulting from phase transformation of an arbitrary combination of phases, such as ferrite phase, austenite phase, pearlite phase, martensite phase, bainite phase, cementite phase may be predicted. Further, in materials other than the iron and steel materials, a material structure resulting from phase transformation of an arbitrary combination of phases may be predicted.

In the embodiment, the method of determining the order of nucleation is not limited to the described one. For instance, in the material structure prediction apparatus 1, sample information indicative of the determined order of nucleation in each typical case may be beforehand stored in a storage medium. The material structure prediction apparatus 1 may retrieve, at the determination of order of nucleation, sample information associated with cases similar to the metal material MT as a prediction target in alloy components and the upstream process (temperature, working rate, etc.). After that, referring to order of nucleation assigned the sample information, the material structure prediction apparatus 1 may determine the order of nucleation. By thus-determining the order of nucleation, the number of calculations by the material structure prediction apparatus 1 or the working amount of the operator can be reduced.

Although in the embodiment, the material structure is predicted by calculating the time evolution of the structure of a precipitated phase, it may be predicted by calculating the time evolution of the structure of a mother phase.

The material structure predicting method of the embodiment is applicable not only to a manufacturing system (such as the hot strip mill line), but also to any system or apparatus. Further, the material structure prediction apparatus 1 is not limited to the above-described configuration. The material structure prediction apparatus 1 may have an arbitrary combination of functions incorporated in other apparatuses. In addition, part of the functions of the material structure prediction apparatus 1 may be incorporated in another apparatus.

A computer constituting the material structure prediction apparatus may have any desired configuration. For instance, the computer includes computing modules, such as various processors, and a storage module, such as a memory or a hard disk device. The computer may further include an input/output module and a display module. The type of the computer is not limited. It may be a microcomputer, a personal computer, or the like.

In the embodiment, part of computing executed by the material structure prediction apparatus (computer) may be performed manually. The principle and theory associated with the prediction method employed in the material structure prediction apparatus utilize laws of nature. Therefore, even when part of processing according to the prediction method of the material structure prediction apparatus is executed manually, the prediction method utilizes laws of nature as a whole.

It is to be noted that the present invention is not restricted to the foregoing embodiments, and constituent elements can be modified and changed into shapes without departing from the scope of the invention at an embodying stage. Additionally, various inventions can be formed by appropriately combining a plurality of constituent elements disclosed in the foregoing embodiments. For example, several constituent elements may be eliminated from all constituent elements disclosed in the embodiments. Furthermore, constituent elements in the different embodiments may be appropriately combined.

What is claimed is:

1. A material structure prediction apparatus predicting a structure of a material that exhibits phase transformation from a mother phase to a precipitated phase in accordance with a temperature variation, the material structure prediction apparatus comprising:
a temperature calculator configured to calculate temperatures at calculation points in a calculation target region of the material, based on a temperature condition for applying the temperature variation to the material;
a nucleation count calculator configured to calculate a nucleation count in the calculation target region, based on the temperatures at the calculation points calculated by the temperature calculator;
a precipitated phase generation point determining module configured to determine, from the calculation points, a precipitated phase generation point where a nucleus of the precipitated phase is generated, based on the nucleation count calculated by the nucleation count calculator;
a grain growth calculator configured to calculate a grain growth of the precipitated phase at the precipitated phase generation point determined by the precipitated phase generation point determining module; and
a material structure prediction module configured to predict the structure of the material, based on the grain growth of the precipitated phase calculated by the grain growth calculator.

2. The material structure prediction apparatus of claim 1, further comprising:
a shape characteristic value calculator configured to calculate a shape characteristic value of crystal grain in the precipitated phase, based on the grain growth of the precipitated phase calculated by the grain growth calculator;
a statistic calculator configured to calculate a statistic of shape characteristic values, based on the shape characteristic value calculated by the shape characteristic value calculator; and
a material quality prediction module configured to predict a quality of the material, based on the statistic calculated by the statistic calculator.

3. The material structure prediction apparatus of claim 2, further comprising:
an actual statistic acquisition module configured to acquire an actual statistic as a statistic of shape characteristic values actually acquired;
a nucleation count calculation correction module configured to correct a calculation formula used to calculate the nucleation count by the nucleation count calculator, based on the statistic calculated by the statistic calculator, and the actual statistic acquired by the actual statistic acquisition module.

4. The material structure prediction apparatus of claim 1, further comprising a material quality evaluation module configured to evaluate a quality of the material, based on the structure of the material predicted by the material structure prediction module.

5. The material structure prediction apparatus of claim 1, wherein the nucleation count calculator is configured to calculate the nucleation count, based on a free energy difference between the mother phase and the precipitated phase and a diffusion coefficient of the mother phase.

6. The material structure prediction apparatus of claim 1, further comprising a nucleation order determination module configured to determine an order of nucleation of the precipitated phase from the mother phase at the calculation points,
wherein the precipitated phase generation point determining module is configured to determine the precipitated phase generation point, using the order of nucleation of the precipitated phase determined by the nucleation order determination module.

7. The material structure prediction apparatus of claim 1, wherein the temperature calculator is configured to calculate the temperatures at the calculation points, based on an actual value of the temperature condition already applied to the material.

8. A method of manufacturing a product from a material that exhibits phase transformation from a mother phase to a precipitated phase in accordance with a temperature variation, the manufacturing method comprising:
controlling a temperature to apply the temperature variation to the material;
calculating temperatures at calculation points in a calculation target region of the material, based on a temperature condition for controlling the temperature;
calculating a nucleation count in the calculation target region, based on the calculated temperatures at the calculation points;
determining, from the calculation points, a precipitated phase generation point where a nucleus of the precipitated phase is generated, based on the calculated nucleation count;
calculating a grain growth of the precipitated phase at the determined precipitated phase generation point;
predicting a structure of the material, based on the calculated grain growth of the precipitated phase;
calculating shape characteristic value of crystal grain in the precipitated phase, based on the predicted structure of the material;
calculating a statistic of shape characteristic values, based on the calculated shape characteristic value; and
manufacturing the product, based on the calculated statistic.

9. The method of claim 8, further comprising calculating a value of transformation-generation heat generated due to the phase transformation of the precipitated phase, based on the calculated grain growth of the precipitated phase,
wherein the controlling the temperature includes using the calculated transformation-generation heat value.

10. The method of claim 8, further comprising:
predicting a quality of the material, based on the calculated statistic,
wherein the manufacturing the product is based on a prediction result of the quality of the material.

11. The method of claim 8, further comprising evaluating a quality of the material, based on the predicted structure of the material.

12. The method of claim 11, further comprising treating the material in a downstream process, based on an evaluation result of the quality of the material.

13. The method of claim 11, further comprising changing the temperature condition, based on an evaluation result of the quality of the material.

14. A material structure prediction method of predicting a structure of a material that exhibits phase transformation from a mother phase to a precipitated phase in accordance with a temperature variation, the material structure prediction method comprising:
calculating temperatures at calculation points in a calculation target region of the material, based on a temperature condition for applying the temperature variation to the material;
calculating a nucleation count in the calculation target region, based on the calculated temperatures at the calculation points;
determining, from the calculation points, a precipitated phase generation point where a nucleus of the precipitated phase is generated, based on the calculated nucleation count;
calculating a grain growth of the precipitated phase at the determined precipitated phase generation point; and
predicting a structure of the material, based on the calculated grain growth of the precipitated phase.

15. The material structure prediction method of claim 14, further comprising:
calculating a shape characteristic value of crystal grain in the precipitated phase, based on the calculated grain growth of the precipitated phase;
calculating a statistic of shape characteristic values, based on the calculated shape characteristic value; and
predicting a quality of the material, based on the calculated statistic.

16. The material structure prediction method of claim 15, further comprising:
acquiring an actual statistic as a statistic of shape characteristic values actually acquired; and
correcting a calculation formula used to calculate the nucleation count, based on the calculated statistic and the acquired actual statistic.

17. The material structure prediction method of claim 14, further comprising evaluating a quality of the material, based on the predicted structure of the material.

18. The material structure prediction method of claim 14, wherein the calculating the nucleation count includes using a free energy difference between the mother phase and the precipitated phase and a diffusion coefficient of the mother phase.

19. The material structure prediction method of claim 14, further comprising determining an order of nucleation of the precipitated phase from the mother phase at the calculation points,
wherein the determining the precipitated phase generation point includes using the determined order of nucleation.

20. The material structure prediction method of claim 14, wherein the calculating temperatures at the calculation points includes using an actual value of the temperature condition already applied to the material.

* * * * *